(12) United States Patent
Wieland et al.

(10) Patent No.: US 11,090,637 B2
(45) Date of Patent: Aug. 17, 2021

(54) FIXED CATALYST BED COMPRISING METAL FOAM BODIES

(71) Applicant: EVONIK OPERATIONS GMBH, Essen (DE)

(72) Inventors: Stefan Wieland, Hanau (DE); Meike Roos, Büdingen (DE); René Poss, Karlsruhe (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/338,044

(22) PCT Filed: Sep. 27, 2017

(86) PCT No.: PCT/EP2017/074491
§ 371 (c)(1),
(2) Date: Mar. 29, 2019

(87) PCT Pub. No.: WO2018/060245
PCT Pub. Date: Apr. 5, 2018

(65) Prior Publication Data
US 2019/0232257 A1    Aug. 1, 2019

(30) Foreign Application Priority Data
Sep. 30, 2016 (EP) ..................... 16191751

(51) Int. Cl.
| | |
|---|---|
| *B01J 25/02* | (2006.01) |
| *B01J 35/04* | (2006.01) |
| *B01J 35/00* | (2006.01) |
| *B01J 35/02* | (2006.01) |
| *B01J 35/10* | (2006.01) |
| *B01J 23/16* | (2006.01) |
| *B01J 8/02* | (2006.01) |
| *B01J 23/70* | (2006.01) |
| *B01J 19/30* | (2006.01) |
| *C07C 29/17* | (2006.01) |
| *B01J 19/24* | (2006.01) |
| *B01J 23/755* | (2006.01) |
| *B01J 21/02* | (2006.01) |
| *C07C 29/153* | (2006.01) |

(52) U.S. Cl.
CPC ............... *B01J 25/02* (2013.01); *B01J 8/02* (2013.01); *B01J 8/0278* (2013.01); *B01J 19/2495* (2013.01); *B01J 19/30* (2013.01); *B01J 21/02* (2013.01); *B01J 23/16* (2013.01); *B01J 23/70* (2013.01); *B01J 23/755* (2013.01); *B01J 35/0026* (2013.01); *B01J 35/026* (2013.01); *B01J 35/04* (2013.01); *B01J 35/1009* (2013.01); *B01J 35/1014* (2013.01); *B01J 35/1019* (2013.01); *B01J 35/1052* (2013.01); *B01J 35/1076* (2013.01); *C07C 29/153* (2013.01); *C07C 29/172* (2013.01); *B01J 2219/30475* (2013.01); *B01J 2219/30491* (2013.01)

(58) Field of Classification Search
CPC . B01J 25/02; B01J 8/0278; B01J 21/02; B01J 23/16; B01J 23/755; B01J 8/02; B01J 8/025; B01J 8/003; C07C 29/153; B10J 35/04; B10J 35/0026; B10J 35/026; B10J 35/1009; B10J 35/1014; B10J 35/1019; B10J 35/1076
See application file for complete search history.

(56) References Cited

U.S. PATENT DOCUMENTS

| | | |
|---|---|---|
| 1,628,190 A | 5/1927 | Raney |
| 1,915,473 A | 6/1933 | Raney |
| 2,139,602 A | 12/1938 | Raney |
| 2,895,819 A | 7/1959 | Fiedler |
| 2,967,893 A | 1/1961 | Hort et al. |
| 2,977,327 A | 3/1961 | Raney |
| 4,049,580 A | 9/1977 | Oden et al. |
| 5,399,793 A | 3/1995 | Vargas et al. |
| 6,262,317 B1 | 7/2001 | Becker et al. |
| 6,969,780 B1 | 11/2005 | Dubner et al. |
| 7,524,996 B2 | 4/2009 | Lorenz et al. |
| 7,538,254 B2 | 5/2009 | Lorenz et al. |
| 7,572,941 B2 | 8/2009 | Lorenz et al. |
| 7,605,292 B2 | 10/2009 | Lorenz et al. |
| 7,612,241 B1 | 11/2009 | White et al. |
| 9,029,290 B2 | 5/2015 | Lee et al. |
| 9,346,079 B2 | 5/2016 | Lee et al. |
| 9,567,276 B2 | 2/2017 | Klasovsky et al. |

(Continued)

FOREIGN PATENT DOCUMENTS

| | | |
|---|---|---|
| CA | 2 823 676 | 8/2012 |
| DE | 102 45 510 | 4/2004 |

(Continued)

OTHER PUBLICATIONS

Liu, Y, et al., Monolithic catalysts with Pd deposited on a structured nickel foam packing, Apr. 7, 2016, Catalysis Today, vol. 273, pp. 34-40 (Year: 2016).*

(Continued)

*Primary Examiner* — Yate' K Cutliff
(74) *Attorney, Agent, or Firm* — Law Office of: Michael A. Sanzo, LLC

(57) ABSTRACT

The present invention relates to a fixed bed of catalytically active metal foam bodies having a volume of not more than 500 mL which consist to an extent of at least 95 wt % of metals. The fixed bed is used for catalytic reactions in a three-phase reaction mixture.

17 Claims, No Drawings

(56) References Cited

U.S. PATENT DOCUMENTS

| | | |
|---|---|---|
| 9,598,537 B2 | 3/2017 | Roos et al. |
| 9,943,818 B2 | 4/2018 | Jin et al. |
| 2002/0151751 A1 | 10/2002 | Ostgard et al. |
| 2002/0193618 A1 | 12/2002 | Ostgard et al. |
| 2003/0047505 A1 | 3/2003 | Grimes et al. |
| 2004/0199019 A1 | 10/2004 | Schmidt |
| 2011/0011772 A1 | 1/2011 | Schmidt |
| 2012/0154983 A1 | 6/2012 | Zhang et al. |
| 2014/0038816 A1 | 2/2014 | Bakker et al. |
| 2014/0221700 A1* | 8/2014 | Radivojevic ............ B01J 25/02 568/885 |
| 2018/0230081 A1 | 8/2018 | Rüfer et al. |
| 2019/0210010 A1 | 7/2019 | Pinkos et al. |
| 2019/0232256 A1 | 8/2019 | Berweiler et al. |
| 2019/0344248 A1 | 11/2019 | Pinkos et al. |
| 2020/0016579 A1 | 1/2020 | Schreiber et al. |
| 2020/0016583 A1 | 1/2020 | Merkel et al. |
| 2021/0032185 A1 | 2/2021 | Roos et al. |

FOREIGN PATENT DOCUMENTS

| | | |
|---|---|---|
| EP | 0 340 970 | 11/1989 |
| EP | 0 807 464 | 11/1997 |
| EP | 2 764 916 | 8/2014 |
| EP | 3 115 106 | 1/2017 |
| GB | 1 242 358 | 8/1971 |
| WO | WO 02/055453 | 7/2002 |
| WO | WO 2005/039764 * | 5/2005 |
| WO | WO 2007/028411 | 3/2007 |
| WO | WO 2008/151614 * | 12/2008 |
| WO | WO 2018/060269 | 4/2018 |
| WO | WO 2021/058702 | 4/2021 |
| WO | WO 2021/058703 | 4/2021 |
| WO | WO 2021/058704 | 4/2021 |
| WO | WO 2021/058705 | 4/2021 |
| WO | WO 2021/058706 | 4/2021 |
| WO | WO 2021/058719 | 4/2021 |

OTHER PUBLICATIONS

Coleman, L. j. i., et al., Evaluaiton of Foam Nickel for the catalytic partial oxidation of methane, Catalysis Letters, 2008, vol. 128 No. 1-2, pp. 144-153 (Year: 2008).*

Luther, E. et al., Nanostructured Metal Foams: Synthesis and Applications, PowderMet2009, Las Vegas, NV, Los Alamos National Laboratory, 12 pages (Year: 2009).*

International Search Report for corresponding PCT/EP2017/074491 filed Sep. 27, 2017.

Written Opinion of the International Searching Authority for corresponding PCT/EP2017/074491 filed Sep. 27, 2017.

International Preliminary Report on Patentability for corresponding PCT/EP2017/074491 filed Sep. 27, 2017.

European Search Report and Search Opinion for corresponding EP 16 19 1751 filed Sep. 30, 2016.

International Search Report for PCT/EP2017/074528 (international counterpart of copending U.S. Appl. No. 16/338,015), filed Sep. 27, 2017.

Written Opinion of the International Searching Authority for PCT/EP2017/074528 (international counterpart of copending U.S. Appl. No. 16/338,015), filed Sep. 27, 2017.

International Preliminary Report on Patentability for PCT/EP2017/074528 (international counterpart of copending U.S. Appl. No. 16/338,015), filed Sep. 27, 2017.

European Search Report and Search Opinion for EP 16 19 1735 (European counterpart of copending U.S. Appl. No. 16/338,015), filed Sep. 30, 2016.

Abdullah, et al., "The use of bulk density measurments as flowability indicators," Powder Technology 102(2):151-165 (May 1999).

Brunauer, et al., "Adsorption of Gases in Multimolecular Layers," J. Am. Chem. Soc. 60:309-319 (Feb. 1938).

Brunet Espinosa, "Ni in CNFs: Highly Active for Nitrate Hydrogenation," ACS Catalysis 6:5432-5440 (2016).

Coleman, et al., "Evaluation of Foam Nickel for the Catalytic Partial Oxidation of Methane," Catalysis Letters 128(1-2):144-153 (Nov. 2008).

Kolaczkowski, et al., "Potential for metal foams to act as structured catalysy supports in fixed-bed reactors," CatalysisToday 273:221-233 (2016).

Li, et al., "Ni—$Al_2O_3$/Ni-Foam Catalyst with Enhanced Heat Transfer for Hydrogenation of $CO_2$ to Methane," AIChE Journal 61(12):4323-4331 (Dec. 2015).

Liu, et al., :Monolithic catalysts with Pd deposited on a structured nickel foam packing, Catalysis Today 273:34-40 (Apr. 2016).

U.S. Appl. No. 16/338,014, filed Mar. 29, 2019, Berweiler.

International Search Report for PCT/EP2020/076823 (international counterpart of copending U.S. Appl. No. 17/059,448), filed Sep. 25, 2020.

Written Opinion of the International Searching Authority for PCT/EP2020/076823 (international counterpart of copending U.S. Appl. No. 17/059,448), filed Sep. 25, 2020.

Non Final Office for copending U.S. Appl. No. 16/338,015, dated Mar. 5, 2021.

U.S. Appl. No. 17/053,340, filed Nov. 5, 2020, Poss.

U.S. Appl. No. 17/059,448, filed Nov. 29, 2020, Roos.

International Search Report for PCT/EP2019/053236 (international counterpart of copending U.S. Appl. No. 16/969,607), filed Feb. 11, 2019.

Written Opinion of the International Searching Authority for PCT/EP2019/053236 (international counterpart of copending U.S. Appl. No. 16/969,607), filed Feb. 11, 2019.

International Preliminary Report on Patentability for PCT/EP2019/053236 (international counterpart of copending U.S. Appl. No. 16/969,607), filed Feb. 11, 2019.

European Search Report and Search Opinion for EP 18 15 6599 (European counterpart of copending U.S. Appl. No. 16/969,607), filed Feb. 14, 2018, with English language machine translation of the Search Opinion attached.

English language machine translation of the European Search Opinion for corresponding EP 16 19 1751, filed Sep. 30, 2016.

English language machine translation of the European Search Opinion for for EP 16 19 1735 international counterpart of copending U.S. Appl. No. 16/338,015), filed Sep. 30, 2016.

Jiang, et al., "Polymer-supported catalysts for clean preparation of n-butanol," Catalysis Science & Technology 4(8):2499-2503 (May 2014).

Petró, et al., "A new alumina-supported, not pyrophoric Raney-type Ni-catalyst," Applied Catalysis A: General 190:73-86.

Ullman's Encyclopedia of Industrial Chemistry, "Metallic Foams" chapter, publisned online on Jul. 15, 2012, DOI: 25 10.1002/14356007.c16_c01.pub2.

Ullmann's Encyclopedia of Industrial Chemistry: G. Eigenberger, W. Ruppel: "Catalytic Fixed-Bed Reactors", Wiley-VCH, online ISBN: 9783527306732 | DOI: 10.1002/14356007; 2012).

Ullmann's Encyclopedia of Industrial Chemistry; D. Sanfilippo, P.N. Rylander: "Hydrogenation and Dehydrogenation", Wiley-VCH, online ISBN: 9783527306732 | DOI: 10.1002/14356007; 2012).

Restriction Requirement dated Oct. 26, 2020, for copending U.S. Appl. No. 16/338,015.

Response to Restriction Requirement filed Dec. 23, 2020, for copending U.S. Appl. No. 16/338,015.

U.S. Appl. No. 16/969,607, filed Aug. 13, 2020, Roos.

* cited by examiner

FIXED CATALYST BED COMPRISING METAL FOAM BODIES

CROSS REFERENCE TO RELATED APPLICATIONS

The present application is US national stage of international application PCT/EP2017/074491, which had an international filing date of Sep. 27, 2017, and which was published on Apr. 5, 2018. Priority is claimed to European application EP 16191751.3, filed on Sep. 30, 2016.

The present invention relates to a fixed catalyst bed of catalytically active metal foam bodies and to a process for catalytic reaction of a mixture of gaseous and liquid reactants in a reactor in which this fixed catalyst bed is arranged.

Heterogeneously catalysed processes are very widely used in industrial practice. Examples of such processes include ammonia, methanol and Fischer-Tropsch syntheses, numerous oxidation and hydrogenation processes and many other reactions. A number of such processes are described extensively in Ullmann's Encyclopedia of Industrial Chemistry in the chapter entitled "Heterogeneous Catalysis and Solid Catalysts, 3. Industrial Applications", published online on 15 Oct. 2011, DOI: 10.1002/14356007.o05_o03.

Many such processes are performed in fixed bed reactors constructed and operated in different ways, see for example in Ullmann's Encyclopedia of Industrial Chemistry in the chapter entitled "Catalytic Fixed-Bed Reactors", published online on 15 Jul. 2012, DOI: 10.1002/14356007.o05_o03.

The development of novel heterogeneous catalysts tailored for specific fields of application represents an important object of modern industrial and academic research. Thus, such heterogeneous catalysts may have various shapes, particle sizes and other material properties as is more particularly described for example in Ullmann's Encyclopedia of Industrial Chemistry in the chapter entitled "Heterogeneous Catalysis and Solid Catalysts, 2. Development and Types of Solid Catalysts", published online on 15 Oct. 2011, DOI: 10.1002/14356007.o05_o02.

Metal foams are well known in the art and are usually used as functional or structure-conferring materials, see also Ullmann's Encyclopedia of Industrial Chemistry, the chapter entitled "Metallic Foams", published online on 15 Jul. 2012, DOI: 10.1002/14356007.c16_c01.pub2. Thus, nickel foams find application for example as electrodes in batteries or as filtration elements.

Catalytic applications of materials based on metal foams are very limited. Metal foam bodies have hitherto usually been employed for heterogeneously catalysed gas phase reactions. These applications include in particular catalytic aftertreatment of exhaust gases from combustion engines, catalytic purification of flue gases, the water-gas shift reaction for producing hydrogen from carbon monoxide and water vapour, or steam reforming of methane. In such applications the dynamic pressure built up in the through flowing reaction medium by the metal foam bodies on account of their high porosity is comparatively low.

Since the porous metal foam bodies known in the prior art are themselves not catalytically active and have an insufficient geometric surface area for heterogeneous catalysis applications, the known applications require that an additional coating for catalytic activation be applied onto the metal foam body. This causes the dynamic pressure to increase significantly relative to the through flowing reaction medium which usually results in significant efficiency losses in heterogeneous catalysis applications.

DE 10245510 A1 discloses an exhaust gas filter for internal combustion engines comprising a foam body employed as a depth filter element which comprises oxidation catalysts distributed in the matrix of the material of construction and can be used for removal and catalytic afterburning of soot particles.

AICHE Journal, 2015, Vol. 61, No. 12, p. 4323-4331 discloses the use of an Ni—$Al_2O_3$/Ni metal foam catalyst as chips having a 16 mm diameter in the gas phase hydrogenation of $CO_2$ to afford methane in a fixed bed reactor. This nickel foam is used as an inert catalyst support onto the surface of which an active Ni/$Al_2O_3$ coating is applied. The thus produced catalyst comprises 12.6 wt % of NiO and 4.2 wt % of $Al_2O_3$.

Catalysis Today, 2016, Vol. 273, p. 221-233 further describes that metal foams generally do not have a sufficiently large area for catalytic applications. There is therefore a need for application of a washcoat having a high surface area and subsequent impregnation with a catalytically active component.

Large industrial scale chemical applications are often reactions of liquid, usually organic compounds with gaseous reactants. Coated catalytic metal foam bodies are not suitable for such applications since the usually relatively high viscosity liquid reactants cannot penetrate into the pores of the metal foam bodies that are narrowed by the coating and accordingly do not come into contact with the catalytically active centres in the pores. Today, such applications usually employ tableted or extruded oxidic moulded bodies previously subjected to catalytic activation by impregnation with noble metal solutions for example. Some of these moulded bodies do exhibit high BET surface areas. However, the available geometric surface area of these oxidic moulded bodies is limited so that the catalytic efficiency of such moulded bodies in reactors which typically have a volume of several cubic metres is restricted by poor mass transfer of the reactants to the catalytically active centre.

ACS Catal. 2016, Vol. 6, p. 5432-5440 discloses nickel foams coated with Carbon Nano Fibres (CNFs) and the use thereof in the hydrogenation of nitrites in a fixed bed reactor in the liquid phase. The catalysts described therein have a relatively high proportion of carbon (27 wt %).

It is an object of the present invention to make possible an efficient catalytic reaction in a three-phase system over a fixed catalyst bed while reducing and/or overcoming both macroscopic mass transfer limitations and limitations resulting from high dynamic pressures over the fixed catalyst bed as are encountered in processes according to the prior art and to provide the appropriate catalyst therefor.

This object is achieved by a fixed bed comprising catalytically active metal foam bodies for catalytic reaction of at least one reactant component in the liquid phase and at least one gaseous component, wherein the catalytically active metal foam bodies have a volume of not more than 500 millilitres, consist to an extent of at least 95 wt % of metals and are arranged as bulk goods in a packed bed.

"Metal foams" is to be understood as meaning rigid metallic foams having a high porosity and numerous interconnections between regions of solid material having an irregular structure. Such metal foams are also known as "cellular metals", the term "metal foams" being more widespread. The term "metal foams" is well established in the technical literature and is more particularly elucidated for example in Ullmann's Encyclopedia of Industrial Chemistry in the chapter entitled "Metallic Foams", published online on 15 Jul. 2012, DOI: 10.1002/14356007.c16_c01.pub2.

"Catalytically active metal foam bodies" in the context of this invention is to be understood as meaning metal foam bodies comprising no additional coatings that could bring about a narrowing of the pores in the metal foam bodies. Catalytically active metal foam bodies in the context of the present invention are catalytically active in the respective target reaction without additional coatings, catalytically active or otherwise. A fixed bed according to the present invention does not contain additional catalytically active coatings either.

The catalytically active metal foam bodies according to the invention are externally discretely bounded, uniformly shaped geometric bodies having a volume that may be calculated exactly from their dimensions. The catalytically active metal foam bodies according to the invention are preferably in the form of cylindrical, ring-shaped, cuboid, parallelepipedal or cubic bodies. The volume of such a body is generally obtained by multiplication of the measurable base area of the body by the likewise measurable height thereof.

A fixed or packed bed in the context of the present invention is to be understood as a conglomeration arranged fixedly in space, i.e. a loose fill of one or more substances consisting of individual bodies, pieces or particles which are spatially fixed in a reactor and/or in a reaction zone.

The fixed bed according to the invention may also comprise, in addition to the catalytically active metal foam bodies, other possibly catalytically inactive constituents, for example fillers or flow-interrupting and/or turbulizing elements.

The fixed bed according to the invention preferably consists to an extent of more than 50 wt %, particularly preferably more than 80 wt %, very particularly preferably more than 95 wt %, of catalytically active metal foam bodies. It is very particularly preferable when the fixed bed of the present invention consists of catalytically active metal foam bodies.

The catalytically active metal foam bodies present in the fixed bed according to the invention consist to an extent of at least 95 wt %, preferably at least 97 wt %, particularly preferably at least 98 wt %, very particularly preferably at least 99 wt %, of metals.

"Metals" is to be understood as meaning elements of the groups IA (except hydrogen), IIA, IB-VIIIB (transition metals), IIIA (except boron), IVA (here: Sn and Pb), VA (here: Bi) and VIA (here: Po) of the Periodic Table of the Elements.

The catalytically active metal foam bodies present in the fixed bed according to the invention preferably comprise one or more metals selected from the group consisting of nickel, cobalt, iron, silver, platinum, chromium, molybdenum and tungsten. It is particularly preferable when the catalytically active metal foam bodies present in the fixed bed according to the invention comprise one or more metals selected from the group consisting of nickel, cobalt and iron. It is very particularly preferable when the catalytically active metal foam bodies present in the fixed bed according to the invention comprise 65 to 98 wt %, preferably 70 to 95 wt %, and particularly preferably 80 to 90 wt % of nickel or cobalt.

The catalytically active metal foam bodies present in the fixed bed according to the invention preferably further comprise up to 25 wt %, particularly preferably 2 to 20 wt %, very particularly preferably 4 to 15 wt %, of aluminium. For most applications embodiments comprising 7 to 13 wt % of aluminium are particularly well suited.

The catalytically active metal foam bodies present in the fixed bed according to the invention further comprise up to 10 wt %, preferably 0.05 to 5 wt %, particularly preferably 0.1 to 2 wt %, of molybdenum (Mo) and/or 0 to 10 wt %, preferably 0.05 to 5 wt %, particularly preferably 1.5 to 3.5 wt %, of one or more elements selected from the group consisting of iron and chromium.

The catalytically active metal foam bodies present in the fixed bed according to the invention moreover comprise less than 5 wt % of oxygen in metal oxide compounds since the presence of such oxidic structures can markedly reduce the catalytic activity of the catalytically active metal foam bodies according to the invention in the relevant target reactions. The catalytically active metal foam bodies according to the invention preferably comprise less than 3 wt %, very particularly preferably less than 1 wt %, of oxides. The oxygen content of particularly well-suited catalytically active metal foam bodies is preferably below 7500 ppm, particularly preferably below 5000 ppm and very particularly preferably below 3000 ppm.

The metal and oxygen contents of the catalytically active metal foam bodies according to the invention may be determined with methods of elemental analysis known in the prior art and familiar to those skilled in the art, metal contents for example—after performance of a suitable wet-chemical digestion process—by means of optical emission spectroscopy (ICP-OES). Oxygen contents are suitably determined by infrared spectroscopy on resulting $CO_2$ for example with an LECO TCH 600 analyser. Prior to determination of the oxygen content of the catalytically active metal foam bodies according to the invention said bodies may need to be specifically deactivated with exclusion of oxygen contamination from the surrounding medium. This applies particularly to embodiments which on account of their catalytic activity may be pyrophoric in air and are thus handled under water as a protective medium before use. Water should initially be removed from such a material gently, for example by careful washing with a dry organic solvent such as ethanol which has a certain capacity for absorbing the residual water in the pores of the catalytically active foam body. Subsequent evacuation removes solvent residues and residual water. Deactivation may be effected by slowly heating to up to 200° C. under vacuum or in a protective gas stream (nitrogen or argon).

In the fixed bed according to the invention the catalytically active metal foam bodies are present as a loose fill material, wherein a volume of 1 L of this loose fill material preferably has a weight of not more than 0.8 kg. A volume of 1 L of this loose fill material particularly preferably has a weight of 0.1 to 0.7 kg, very particularly preferably 0.2 to 0.6 kg. Accordingly, the catalytically active metal foam bodies present in the fixed bed according to the invention preferably have a bulk density of not more than 0.8 kg/L, particularly preferably from 0.1 to 0.7 kg/L, very particularly preferably from 0.2 to 0.6 kg/L.

Bulk density $d_{sch}$, sometimes also referred to as poured density of a solid, is the ratio of mass to volume of a mixture of a solid, which may be granular, and air which fills the cavities between the particles of the solid/the solid bodies. This parameter which is commonly used by those skilled in the art may be determined by means of a measuring cylinder and a balance by determining the mass ($M_F$) of a defined loose fill volume of solid ($V_F$).

$$d_{sch}=M_F/V_F$$

The bulk density can be determined by slow addition of a defined amount of the drop-wet catalyst to a 1 L standard measuring cylinder filled with water. After settling of the catalyst is complete, the volume of the catalyst bed is read off the scale. The bulk density $d_{sch}$ is calculated according to the equation $$d_{sch}=M_F/V_F$$

where $M_F$ is the amount of catalyst used in the dry mass and $V_F$ is the volume of the bed observed under water. The dry mass of the activated catalyst can be determined by comparative weighing of a container of defined volume, which is filled with water and catalyst, to a container of the same volume, which is filled only with water. The mass of the dry catalyst is given by the difference of the two weights multiplied by a density factor k, which is derived from the quotient of the density of the dry catalyst and the difference in density between the dry catalyst and water. Density factors can be taken directly from the technical literature and/or the handling instructions of the manufacturers and distributors of catalysts of the Raney type and are typically about 1.2. The volume of the catalyst bed is directly accessible to those skilled in the art by reading off the scale of the measuring cylinder used. The method is independent of the particle size of the Raney type catalyst, i.e. independent of whether they are beds of granular or foam material or are powder catalysts under water.

The catalytically active metal foam bodies present in the fixed bed according to the invention have a volume of not more than 500 millilitres (mL). The geometric shape and size of the catalytically active metal foam bodies according to the invention and thus the volume thereof is controllable and may be adapted to the conditions prevailing in the employed reactor to maintain optimal conditions for mass transfer at minimum counterpressure on the reaction medium. In preferred embodiments of the fixed bed according to the invention the catalytically active metal foam bodies have a volume of not more than 200 mL, particularly preferably from 0.02 to 100 mL and very particularly preferably from 0.02 to 50 mL.

The catalytically active metal foam bodies present in the fixed bed according to the invention are preferably in the form of cylindrical, ring-shaped, cuboid, parallelepipedal or cubic bodies. These are preferably produced from metal foam sheets having an edge length of at least 300 mm and a thickness of 0.5 to 10 mm, preferably of 1 to 5 mm. From these metal foam sheets it is possible to obtain for example by laser cutting/laser beam cutting smaller geometrical bodies preferably having a cuboid or parallelepipedal shape and a maximum edge length of not more than 50 mm, preferably of not more than 25 mm and particularly preferably of not more than 10 mm. Cubic bodies having an edge length of 0.5 to 10 mm, preferably of 1 to 5 mm, may be produced in the same way. Ring-shaped bodies may also be prepared by this mode of production. The external diameter thereof is preferably less than 100 mm, particularly preferably less than 50 mm and very particularly preferably less than 20 mm. The internal diameter is to be chosen such that a ring width of preferably 2 to 80 mm is formed.

The catalytically active metal foam bodies in the fixed bed according to the invention may have a cylindrical shape, wherein the cylindrical shape has been generated by winding a metal foam sheet. A fixed bed according to the invention composed of cylindrically shaped catalytically active metal foam bodies having a volume of 25 to 500 millilitres is particularly suitable in large industrial scale fixed bed reactors having total volumes of several cubic metres. Cylindrical metal foam bodies may likewise be prepared from metal foam sheets having an edge length of at least 300 mm and a thickness of 0.5 to 10 mm, preferably of 1 to 5 mm. To this end the metal foam sheets are wound up along their long edge until a cylindrical "roll" having the desired target diameter is formed and then brought to the desired length by laser cutting/laser beam cutting for example. To improve mass transfer and increase the turbulence of the reaction medium flowing through the catalytically active metal foam body in use the metal foam sheet may be corrugated—similarly to corrugated sheet metal—before winding so that laminar flow paths are minimized in the resulting cylindrical metal foam body.

The catalytically active metal foam bodies present in the fixed bed according to the invention have a macroscopic foam structure. Porous metal foam structures comprising many cavities may for example be formed by action of gases on a liquefied metal and subsequent cooling. A further option for achieving such structures is using organic foam structures as a template for the application of a metal and subsequently removing the organic template by incineration. The macroscopic pores present in the metal foam bodies according to the invention preferably have a size in the range from 100 to 5000 µm, particularly preferably from 200 to 2500 µm, particularly preferably from 400 to 1200 µm. The size of the macroscopic pores may be determined using for example a method described in "The Guide 2000 of Technical Foams", book 4, part 4, pages 33-41. The size of the macroscopic pores may be determined by optical measurement of the pore diameter of a selected pore. This measurement is repeated for at least 100 different pores and an average pore diameter is calculated therefrom as the analytical result.

The catalytically active metal foam bodies present in the fixed bed according to the invention preferably have a BET surface area of 1 to 200 $m^2/g$, particularly preferably 10 to 120 $m^2/g$, very particularly preferably 70 to 100 $m^2/g$. The specific surface area also referred to as BET surface area for simplicity is determined to DIN 9277 by nitrogen adsorption according to the Brunauer-Emmett-Teller method as described in J. Am. Chem. Soc. 1938, Vol. 60, p. 309-319.

The catalytically active metal foam bodies present in the fixed bed according to the invention are obtained for example by chemical leaching of at least one metal out of an at least binary metal alloy.

"Raney-type" activated nickel or cobalt catalysts, also known as Raney catalysts, are especially suitable for use as catalytically active metal foam bodies in a fixed bed according to the invention. The preferred production of such a catalytically active metal foam body is therefore described hereinbelow with reference to the example of a catalytically activated nickel foam body. The elucidated production steps may be applied to other metal foam bodies not explicitly described here with suitable adaptation of the process parameters.

To produce a catalytically active nickel foam body a commercially available nickel foam is treated with an adhesion promoter and coated with aluminium powder. Any adhesion promoter which improves adhesion between metals and organic materials may be employed. Polyethyleneimine solution for example is suitable.

The nickel foam retains its ductility in these process steps and may for example be subjected to forming in a suitable manner for production of cylindrical bodies. In a subsequent heat treatment with exclusion of oxygen initially moisture and organic chemical residues of the adhesion promoter are specifically removed. aluminium is then dissolved in the nickel foam to form intermetallic phases. The spatial structure of the resulting nickel/aluminium alloy foam including the pore structure (geometry, porosity, dimensions) corresponds to that of the employed nickel foam whose original character is retained in its entirety in this process step. The resulting nickel/aluminium alloy foam accordingly comprises no pore-narrowing coating.

The heat treatment is preferably performed in a temperature range between 500° C. and 1000° C., particularly preferably between 600° C. and 750° C. The heat treatment is effected in an atmosphere of oxygen-free inert gas to prevent formation of disruptive oxidic phases and layers.

After the heat treatment a comminution and/or separation of the material for example by laser cutting/laser beam cutting may be effected provided this has not already taken place in a forming step prior to the heat treatment.

Catalytically active nickel foam bodies according to the invention are prepared from the thus obtained nickel/aluminium shaped bodies by leaching at least a portion of the aluminium present therein. Employed therefor are aqueous basic solutions, preferably alkali metal hydroxide solutions, wherein the alkali metal hydroxide is selected from the group consisting of sodium hydroxide, potassium hydroxide or lithium hydroxide. Aqueous sodium hydroxide solution is particularly preferred. The concentration of the aqueous alkali metal hydroxide solution employed in this process step is generally between 0.1 and 60 wt %. The leaching of the aluminium is preferably effected with a 5 to 50 wt %, particularly preferably 5 to 35 wt %, aqueous sodium hydroxide solution at a temperature of 20° C. to 100° C., preferably at 40° C. to 85° C., particularly preferably at 50° C. to 80° C. The leaching times to be used here, i.e. the reaction times of the sodium hydroxide solution with the aluminium-modified nickel metal foam, may be between 2 and 240 minutes.

In the above described catalytically active metal foam bodies present in the fixed bed according to the invention the macroscopic foam structure of the originally employed metal foam is retained. The at least partial leaching of the aluminium out of the Ni/Al alloy in the above described example is effected in near-surface regions where a high-porosity, catalytically active nickel structure is generated. The BET surface area of the thus obtained catalytically active nickel foam body is preferably greater than that of the employed metal foam prior to activation.

The present invention further provides a process for catalytic reaction of at least one reactant component in the liquid phase and at least one gaseous component in the presence of a fixed bed according to the invention comprising catalytically active metal foam bodies, wherein the catalytically active metal foam bodies have a volume of not more than 500 millilitres and consist to an extent of at least 95 wt % of metals.

The above described fixed bed according to the invention is used for catalytic reaction of at least one reactant component in the liquid phase and at least one gaseous component. Such three-phase reactions may be performed as a discontinuous (batch) or continuous operation.

The process according to the invention is preferably carried out as a continuous operation.

All reactor types which allow the spatial fixing of the fixed bed according to the invention during operation may be employed in the process according to the invention. Thus for example stirred tank reactors, fixed bed reactors or other apparatuses known to one skilled in the art may be used.

When the process according to the invention is performed in a stirred tank reactor the fixed bed according to the invention is preferably in a retaining device. Said device is preferably arranged in proximity to the stirrer shaft, wherein the arrangement is effected such that the stirrer generates a flow of the reaction mixture through the fixed bed that has been introduced into the retaining device.

The process according to the reaction is preferably carried out as a continuous operation in a fixed bed reactor, for example in a trickle bed reactor or liquid-filled reactor or in another fixed bed reactor type known in the art. All suitable reactor types may be operated in a "once through" mode, in which the reactants (feed) are introduced into the reactor while the product mixture is removed after reaction in the fixed bed according to the invention. Alternatively, a portion of the product mixture may be passed from the reactor back into the reaction zone (recirculating stream). In such a recirculating regime (recycling mode), the weight ratio of feed to recirculating stream is 0.025 to 0.25, preferably 0.05 to 0.15, particularly preferably 0.05 to 0.1.

The process according to the invention is preferably performed as a continuous operation in a reactor with a total volume of at least 0.5 $m^3$, particularly preferably in a reactor having a total volume of 1 to 500 $m^3$ and very particularly preferably 5 to 100 $m^3$.

A catalytic reaction as per the process according to the invention is preferably a hydrogenation of at least one substance which is present as the reactant component in the liquid phase and comprises at least one unsaturated C—C bond and/or at least one functional group. Hydrogen is employed as the gaseous component.

The reactant component which is used for the hydrogenation and is present in the liquid phase is preferably at least one substance selected from the group consisting of alkenes, alkynes, unsaturated alcohols, aromatic compounds, organic nitro and nitroso compounds, organic isocyanates, organic cyanide compounds, aldehydes and ketones. The catalytic reaction in the process according to the invention may in particular be the hydrogenation of a substance from the group of sugars, wherein the sugar for hydrogenation is then supplied to the fixed bed according to the invention optionally in aqueous solution.

The inventive fixed bed of catalytically active metal foam bodies is further suitable for dehydrogenation of alcohols to afford aldehydes and/or ketones or for reductive amination of aldehydes and/or ketones. The fixed bed according to the invention may also be employed for the synthesis of fatty amines or for reductive alkylation of organic compounds.

Further fields of application of the fixed bed according to the invention are heterogeneously catalysed reactions in the gas phase such as the oxidation of ethene to afford ethylene oxide or ammonia oxidation according to the principle of the Ostwald process.

The invention is more particularly elucidated hereinbelow with reference to examples. The production and use of a loose fill fixed bed according to the invention is shown by way of example in the hydrogenation of 1,4-butynediol to afford butanediol.

EXAMPLE 1

A nickel foam commercially available in rolls and having a thickness of 1.9 mm, a width of 300 mm and an average pore size of 580 μm was sprayed with a commercially available adhesion promoter solution, coated with aluminium powder and subjected to a heat treatment at around 700° C. in the absence of oxygen. After cooling the thus obtained material was cut with a laser into square pieces having an edge length of 2 mm×2 mm and a thickness of 1.9 mm.

To achieve catalytic activation the resulting loose fill material was arranged in a loose fill fixed bed and subjected to wet-chemical aftertreatment by pumping a 10 wt % aqueous sodium hydroxide solution therethrough at 80° C. to 90° C. for a duration of 70 minutes and subsequently washing with water until a pH of the washing solution after pumping through the loose fill fixed bed of <10 had been achieved.

COMPARATIVE EXAMPLE

Large industrial scale hydrogenation of 1,4-butynediol (BYD) to afford 1,4-butanediol employs pellet-type activated nickel catalysts, as is disclosed for example in DE 2004611 A. Such a catalyst was produced as comparative material. To this end by melting nickel and aluminium an alloy consisting of 50 wt % nickel and 50 wt % aluminium was produced, subjected to mechanical comminution and sieved to obtain a grain fraction having an average grain size of 2 mm. This alloy pellet fraction was catalytically activated in a loose fill fixed bed by pumping a 10 wt % aqueous sodium hydroxide solution therethrough at 60° C. for a duration of 60 minutes and subsequently washing with water until a pH of the resulting washing solution of <10 had been achieved.

EXAMPLE 2

The inventive catalytically active metal foam bodies from example 1 and the prior art catalyst from the comparative example were tested in a continuous fixed bed plant for their hydrogenation activity for the hydrogenation of butyne-1,4-diol (BYD) to afford 1,4-butanediol. To this end both the inventive catalytically activated metal foam bodies and the prior art pellet catalyst from the comparative example were each charged into a tubular reactor having an internal diameter of 12 mm and a length of 175 mm and an effective volume of 18 ml. The volume of the fixed catalyst bed charged was 10 ml. The tubular reactor was arranged in a GC oven for heating. Located upstream of the reactor was a tube filled with glass spheres which as an inlet sector into the reactor served to heat and premix the reactants.

At a hydrogen pressure of 275 bar the reactor was continuously supplied with a liquid feed stream consisting of 50 wt % water, 20 wt % butyne-1,4-diol and 30 wt % 1,4-butanediol in which by addition of dilute sodium hydroxide solution a pH of 7.3 to 7.5 had been established. The liquid hourly space velocity (LHSV) was 2.75 h$^{-1}$ for the chosen mode of operation. The reactor was heated to 120° C.

During continuous operation of the reactor over several days samples of the reaction product were withdrawn and their composition analysed by gas chromatography at regular intervals. The results of these continuous tests are summarized in table 1.

TABLE 1

| | Proportion of 1,4-butanediol in the reaction product | |
|---|---|---|
| Test running time in hours | Catalyst from comparative example | Catalyst from example 1 |
| 0 | 55.6% | 55.6% |
| 4 | 70.5% | 65.2% |
| 28 | 75.4% | 80.7% |
| 55 | 66.3% | 93.1% |

It was found that higher catalytic activities were achieved over the inventive fixed bed of catalytically active nickel foam bodies than over the prior art fixed bed. The inventive fixed bed of catalytically active nickel foam bodies furthermore showed markedly improved uptimes, i.e. was able to be operated continuously at a higher activity level for considerably longer than the prior art catalyst fixed bed.

The invention claimed is:

1. A fixed bed comprising catalytically active metal foam bodies for catalytic reaction of at least one reactant component in a liquid phase and at least one gaseous component, wherein the catalytically active metal foam bodies have a volume of not more than 500 millilitres, comprise at least 95 wt % of metals and are arranged as bulk goods in a packed bed and wherein the catalytically active metal foam bodies have a BET surface area of 1 to 200 m$^2$/g and an oxygen content of not more than 7500 ppm.

2. The fixed bed of claim 1, wherein the catalytically active metal foam bodies comprise one or more metals selected from the group consisting of: nickel, cobalt, iron, silver, platinum, chromium, molybdenum and tungsten.

3. The fixed bed of claim 2, wherein the catalytically active metal foam bodies further comprise up to 25 wt % of Al.

4. The fixed bed of claim 1, wherein the catalytically active metal foam bodies are present in the fixed bed as a loose fill material, wherein a volume of 1 L of this loose fill material has a weight of not more than 0.8 kg.

5. The fixed bed of claim 1, wherein the catalytically active metal foam bodies are in the form of cylindrical, ring-shaped, cuboid, parallelepipedal or cubic bodies.

6. The fixed bed of claim 5, wherein the catalytically active metal foam bodies have a cylindrical shape.

7. The fixed bed of claim 6, wherein the cylindrically shaped catalytically active metal foam bodies are corrugated.

8. The fixed bed of claim 1, wherein the catalytically active metal foam bodies have macroscopic pores having a size in the range from 100 to 5000 μm.

9. A process for catalytic reaction of at least one reactant component in a liquid phase and at least one gaseous component wherein said process is carried out using the fixed bed of claim 1.

10. The process of claim 9, wherein the process is performed as a continuous operation in a reactor having a total volume of at least 0.5 m$^3$.

11. The process of claim 9, wherein the catalytic reaction is a hydrogenation, wherein hydrogen is the gaseous component and the reactant component in the liquid phase comprises at least one unsaturated C—C bond and/or at least one functional group.

12. The process of claim 9, wherein the catalytic reaction is a hydrogenation of at least one substance selected from the group consisting of: alkenes, alkynes, unsaturated alcohols, aromatic compounds, organic nitro and nitroso compounds, organic isocyanates, organic cyanide compounds, aldehydes and ketones; and wherein hydrogen is employed as the gaseous component.

13. The process of claim 9, wherein the catalytic reaction is the hydrogenation of a sugar.

14. The process of claim 9, wherein the catalytic reaction is a dehydrogenation of alcohols to produce aldehydes and/or ketones or a reductive amination of aldehydes and/or ketones.

15. The process of claim 9, wherein the catalytic reaction is a synthesis of fatty amines or a reductive alkylation of organic compounds.

16. The fixed bed of claim 2, wherein the catalytically active metal foam bodies are present in the fixed bed as a loose fill material, wherein a volume of 1 L of this loose fill material has a weight of not more than 0.8 kg.

17. The fixed bed of claim 16, wherein the catalytically active metal foam bodies have macroscopic pores having a size in the range from 100 to 5000 μm.

* * * * *